United States Patent [19]

Coates et al.

[11] Patent Number: 5,254,571
[45] Date of Patent: Oct. 19, 1993

[54] CHEMICAL COMPOUNDS

[75] Inventors: William J. Coates, Welwyn Garden City; Sean T. Flynn, St. Albans, both of England

[73] Assignee: Smith Kline & French Laboratories Ltd., Welwyn Garden City, England

[21] Appl. No.: 951,363

[22] Filed: Sep. 25, 1992

Related U.S. Application Data

[63] Continuation of Ser. No. 760,849, Sep. 17, 1991, abandoned, which is a continuation of Ser. No. 339,733, Apr. 18, 1989, abandoned.

[30] Foreign Application Priority Data

Apr. 21, 1988 [GB] United Kingdom ............... 8809481

[51] Int. Cl.$^5$ .................... C07D 213/62; A61K 31/44
[52] U.S. Cl. ..................................... 514/344; 514/350; 514/340; 514/345; 514/349; 546/288; 546/298; 546/276; 546/301; 546/297
[58] Field of Search ............... 514/344, 350, 340, 345, 514/349; 546/288, 298, 276, 301, 297

[56] References Cited

U.S. PATENT DOCUMENTS

| 3,703,582 | 11/1972 | Shen et al. ........................... 546/113 |
| 4,393,058 | 7/1983 | Makabe et al. ..................... 514/206 |
| 4,820,719 | 4/1989 | Gleason et al. ..................... 514/381 |

FOREIGN PATENT DOCUMENTS

| 296731 | 6/1987 | European Pat. Off. |
| 2070606 | 9/1981 | United Kingdom. |
| 8304024 | 11/1983 | World Int. Prop. O. |

OTHER PUBLICATIONS

Corey et al., "Stereospecific Total Synthesis of a Slow Reacting Substance of Anaphylaxis, Leukotriene C-1", J. Am. Chem. Soc., 102, 1436 (1980).
Chong et al., "Nucleophilic Openings of 2,3-Epoxy Acids and Amides Mediated by Ti(O-i-Pr)$_4$. Reliable C'3 Selectivity", J. Org. Chem. 50, 1560 (1985).
Chemical Abstracts 36:2846$^6$. Fourneau et al, J. Pharm. Chim., 19, 49 (1934).
Fourneau et al., "Action de l'ammoniac et des amines sur less esters phenylglycidiques", Bull. Soc. Chim., 7, 593 (1940). Chemical Abstracts 28:5179$^7$.
Tung et al., "Epoxide Studies. I. The Ring Opening of cis- and trans-N,N-Diethylphenylglycidamine" J. Org. Chem. 28, 2009 (1963).
Tung et al., "The Darzens Condensation II. Reaction of Chloroacetamides with Aromatic Aldehydes", J. Org. Chem., 28, 1514 (1963).
Richter et al., "Synthesis of (±)-Cyclopenine Derivatives", Pharmazie, 29, 506 (1974).
Baldas et al., "Mass spectrometric Studies II. Beta-phenylglycidic Esters and Amides", Aus. J. Chem., 20, 2655 (1967).
Zheglova et al., J. Molecular Structure, 115, 371 (1984).
Abramovitch et al., J. Chem. Soc. (Chem. Comm.), 149 (1978).
Ames et al., J. Chem. Soc. (Perkin I) 10, 1073 (1976).
Duguay et al., Bull. Chem. Soc. Fr., 12, 4485 (1967).
Lockhart et al., J. Chem. Soc., 3610 (1965).

Primary Examiner—Jane T. Fan
Attorney, Agent, or Firm—Charles M. Kinzig; Stephen Venetianer; Edward T. Lentz

[57] ABSTRACT

This invention relates to phenylpyridone derivatives which have bronchodilator and anti-allergic activities. A compound of the invention is 6-(2-propoxyphenyl)-1,2-dihydro-2-oxopyridine-3-carboxamide.

13 Claims, No Drawings

CHEMICAL COMPOUNDS

This is a Continuation of application Ser. No. 07/760,849 filed Sep. 17, 1991 now abandoned which is a continuation of application Ser. No. 07/339,733 filed Apr. 18, 1989 now abandoned.

The present invention relates to phenylpyridone derivatives. This invention further relates to intermediates in their preparation, to pharmaceutical compositions containing them and a method of effecting bronchodilatation or of combatting allergic disease by administering them.

The compounds of this invention are inhibitors of a calmodulin insensitive cyclic GMP phosphodiesterase and are of use in combatting such conditions where such inhibition is thought to be beneficial. The prime activities of the compounds of this invention are bronchodilatation and anti-allergic activity. The compounds of this invention are therefore of use in combatting chronic reversible obstructive lung diseases such as asthma and bronchitis and in combatting allergic diseases such as allergic asthma, allergic rhinitis, urticaria and irritable bowel syndrome. Furthermore the compounds of this invention are vasodilators and are therefore of value in combatting angina, hypertension and congestive heart failure. The compounds of this invention also exhibit anti-inflammatory activity.

GB patent application 2070606 discloses as cardiotonic agents compounds of the formula (A):

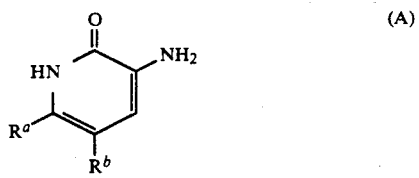

wherein $R^a$ is inter alia phenyl optionally substituted by $C_{1-4}$alkoxy and $R^b$ is inter alia hydrogen or $C_{1-4}$alkyl. None of the compounds of the present invention are specifically disclosed.

U.S. Pat. No. 3703582 discloses compounds of the formula (B):

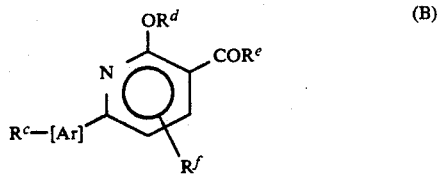

wherein [Ar] is inter alia phenyl, $R^c$ is inter alia alkoxy, $R^d$ is inter alia hydrogen, $R^e$ is inter alia hydroxy, alkoxy, amino, alkylamino or dialkylamino and $R^f$ is inter alia hydrogen or alkyl. The compounds are described as having anti-inflammatory, anti-pyretic, analgesic, diuretic, anti-fibrinolytic and hypoglycemic activities. Compounds of the formula (B) that are specifically disclosed include compounds wherein [Ar] is phenyl, $R^c$ is 2-methoxy, $R^d$ is hydrogen, $R^e$ is —CN, —CO$_2$H or —CO$_2$CH$_2$CH$_3$ and $R^f$ is hydrogen or 5-methyl. None of the compounds of the present invention are specifically disclosed.

According to the present invention there is provided compounds of the formula (1) :

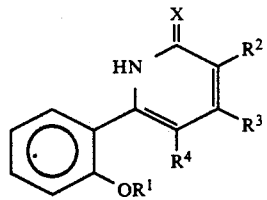

and pharmaceutically acceptable salts thereof, wherein
X is O or S;
$R^1$ is $C_{1-6}$alkyl, $C_{2-6}$alkenyl, $C_{3-5}$cycloalkyl$C_{1-4}$alkyl, or $C_{1-4}$alkyl substituted by 1 to 6 fluoro groups;
$R^2$ is hydrogen, —CN, —CONR$^5$R$^6$, —CO$_2$R$^7$, 5-tetrazolyl, —NO$_2$, —NH$_2$ or —NHCOR$^8$ wherein R$^5$, R$^6$, R$^7$ and R$^8$ are independently hydrogen or $C_{1-4}$alkyl;
$R^3$ is hydrogen or $C_{1-4}$alkyl; and
$R^4$ is hydrogen or $C_{1-4}$alkyl;
with the proviso that $R^1$ is not methyl when $R^2$ is —CO$_2$H, —CO$_2$CH$_2$CH$_3$ or —CN, X is O, $R^3$ is hydrogen and $R^4$ is hydrogen or methyl.

Suitably X is S. Preferably X is O.

Suitably $R^1$ is $C_{2-6}$alkyl for example ethyl, n-propyl, isopropyl, butyl, isobutyl, pentyl or hexyl.

Suitably $R^1$ is $C_{3-5}$alkenyl for example allyl, butenyl or pentenyl.

Suitably $R^1$ is cyclopropylmethyl.

Examples of $C_{1-4}$alkyl substituted by 1 to 6 fluoro groups include —CF$_3$, —CH$_2$CF$_3$ or —CF$_2$CHFCF$_3$.

Preferably $R^1$ is n-propyl.

Suitably $R^2$ is hydrogen, —CN, 5-tetrazolyl or —NO$_2$.

Suitably $R^2$ is —CONR$^5$R$^6$ wherein —NR$^5$R$^6$ is amino.

Suitably $R^2$ is —CO$_2$R$^7$ wherein R$^7$ is methyl.

Suitably $R^3$ is hydrogen or methyl.

Suitably $R^4$ is hydrogen or methyl.

Specific compounds of this invention are :
3-cyano-6-(2-propoxyphenyl)-2(1H)-pyridinone,
6-(2-propoxyphenyl)-1,2-dihydro-2-oxopyridine-3-carboxamide
6-(2-propoxyphenyl)-1,2-dihydro-2-oxopyridine-3-carboxylic acid,
methyl 6-(2-propoxyphenyl)-1,2-dihydro-2-oxopyridine-3-carboxylate,
6-(2-propoxyphenyl)-3-(1-tetrazol-5-yl)-2(1H)-pyridinone,
6-(2-propoxyphenyl)-2(1H)-pyridinone,
3-nitro-6-(2-propoxyphenyl)-2(1H)-pyridinone,
3-cyano-6-(2-ethoxyphenyl)-2(1H)-pyridinone,
3-amino-6-(2-propoxyphenyl)-2(1H)-pyridinone,
3-cyano-4-methyl-6-(2-propoxyphenyl)-2(1H)-pyridinone,
3-cyano-5-methyl-6-(2-propoxyphenyl)-2(1H)-pyridinone,
3-cyano-6-(2-(1,1,2,3,3,3-hexafluoropropoxy)phenyl-2(1H)-pyridinone,
3-cyano-6-(2-propoxyphenyl)-2(1H)-pyridinethione,
1,2-dihydro-4-methyl-2-oxo-6-(2-propoxyphenyl)pyridine-3-carboxylic acid,
methyl 1,2-dihydro-4-methyl-2-oxo-6-(2-propoxyphenyl)-pyridine-3-carboxylate,
1,2-dihydro-4-methyl-2-oxo-6-(2-propoxyphenyl)pyridine-3-carboxamide,
3-cyano-6-(2-cyclopropylmethoxyphenyl)-2(1H)-pyridinone, 6-(2-butoxyphenyl)-3-cyano-2(1H)-pyridinone,
6-(2-allyloxyphenyl)-3-cyano-2(1H)-pyridinone,
3-cyano-6-[2-(2-methylpropoxy)phenyl]-2(1H)-pyridinone,
6-(2-ethoxyphenyl)-1,2-dihydro-2-oxopyridine-3-carboxamide,
6-(2-cyclopropylmethoxyphenyl)-1,2-dihydro-2-oxopyridine-3-carboxamide,
6-(2-butoxyphenyl)-1,2-dihydro-2-oxopyridine-3-carboxamide, and
1   6-[2-(2-methylpropoxyphenyl)-1,2-dihydro-2-oxopyridine-3-carboxamide, and pharmaceutically acceptable salts thereof.

This invention covers all tautomeric and optical isomeric forms of compounds of formula (1).

Compounds of the formula (1) may form pharmaceutically acceptable salts with metal ions, such as alkali metals for example sodium and potassium, or with an ammonium ion.

In order to use a compound of the formula (1) or a pharmaceutically acceptable salt thereof for the treatment of humans and other mammals it is normally formulated in accordance with standard pharmaceutical practice as a pharmaceutical composition.

Compounds of formula (1) and their pharmaceutically acceptable salts may be administered in standard manner for the treatment of the indicated diseases, for example orally, parenterally, transdermally, rectally, via inhalation or via buccal administration.

Compounds of formula (1) and their pharmaceutically acceptable salts which are active when given orally or via buccal administration can be formulated as liquids, syrups, tablets, capsules and lozenges. An oral liquid formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, celluloses, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of formula (1) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane, or are in the form of a powder for insufflation.

Preferably the composition is in unit dosage form, for example a tablet, capsule or metered aerosol dose, so that the patient may administer to himself a single dose.

Each dosage unit for oral administration contains suitably from 0.001 mg/Kg to 30 mg/Kg, and preferably from 0.005 mg/Kg to 15 mg/Kg, and each dosage unit for parenteral administration contains suitably from 0.001 mg/Kg to 120 mg/Kg, of a compound of formula (1) or a pharmaceutically acceptable salt thereof calculated as the free base.

The daily dosage regimen for oral administration is suitably about 0.001 mg/Kg to 120 mg/Kg, of a compound of formula (1) or a pharmaceutically acceptable salt thereof calculated as the free base. The daily dosage regimen for parenteral administration is suitably about 0.001 mg/Kg to 40 mg/Kg, for example about 0.005 mg/Kg to 10 mg/Kg, of a compound of the formula (1) or a pharmaceutically acceptable salt thereof calculated as the free base. The active ingredient may be administered as required for example from 1 to 8 times a day or by infusion. The compositions of the invention are bronchodilators and are useful in chronic reversible obstructive lung disease for example asthma and bronchitis. In addition the compositions of the present invention have anti-allergic activity and are useful in combatting allergic diseases such as allergic asthma, allergic rhinitis, urticaria and irritable bowel syndrome. The compositions of the present invention also have vasodilator activity and are of use in the treatment of angina, hypertension and congestive heart failure. Such conditions can be treated by administration orally, topically, rectally, parenterally or by inhalation. For administration by inhalation dosages are controlled by a valve, are administered as required and for an adult are conveniently in the range 0.1-5.0 mg of a compound of the formula (1) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (1) are bronchodilators such as sympathomimetic amines for example isoprenaline, isoetharine, sulbutamol, phenylephrine and ephedrine or xanthine derivatives for example theophylline and aminophylline, anti-allergic agents for example disodium cromoglycate, histamine $H_1$-antagonists, vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (1) or pharmaceutically acceptable salts thereof, can be prepared by a process which comprises :

a) reacting a compound of the formula (2):

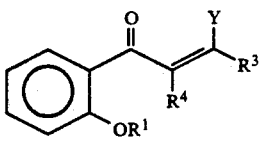

wherein $R^1$, $R^3$ and $R^4$ are as hereinbefore defined and Y is a displaceable group,
with a compound of the formula (3):

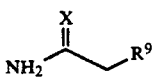

wherein X is as hereinbefore defined and $R^9$ is a group $R^2$ as hereinbefore defined or a precursor thereof;
b) reacting a compound of the formula (4):

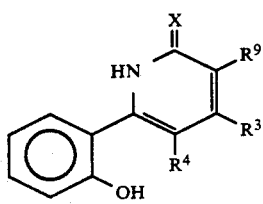

wherein X, $R^3$, $R^4$ and $R^9$ are as hereinbefore defined, with a reagent that provides an $R^1$ group, and thereafter where necessary:
converting a group $R^9$ to a group $R^2$;
optionally forming a pharmaceutically acceptable salt.

Suitably Y is hydroxy or a derivative thereof for example Y is protected hydroxy such as silyloxy, an acid residue (for example $C_{1-6}$alkanoyloxy) or an ether residue (for example methoxy or ethoxy). Alternatively Y is a secondary amino group, for example di-$C_{1-6}$alkylamino such as dimethylamino or a cyclic amino group such as piperidino, pyrrolidino or morpholino. Preferably Y is hydroxy or dimethylamino.

Suitably an alkali metal (e.g. sodium) salt of a compound of the formula (2) wherein Y is hydroxy is treated with a compound of the formula (3) under mildly alkaline aqueous conditions, for example in water in the presence of piperidine and glacial acetic acid, at an elevated temperature e.g. 30°-200° C., preferably at the reflux temperature of the reaction mixture.

Alternatively a compound of the formula (2) wherein Y is a secondary amino group, for example dimethylamino, is treated with a compound of the formula (3) in a suitable solvent such as dimethylformamide, a $C_{1-4}$alkanol or pyridine at an elevated temperature e.g. 30°-200° C., preferably at the reflux temperature of the reaction mixture optionally in the presence of a base such as pyridine or an alkali metal alkoxide, e.g. sodium methoxide.

Suitably a compound of the formula (4) is treated with a reagent that provides an $R^1$ group in an organic solvent such as acetone, dimethylformamide, dimethylsulphoxide or a $C_{1-4}$alkanol such as methanol or ethanol in the presence of a base such as potassium carbonate, potassium hydroxide, sodium hydroxide, potassium tert-butoxide or sodium hydride at ambient or elevated temperature e.g 30°-100° C. An example of a reagent that provides an $R^1$ group is a compound of the formula $R^1Z$ wherein $R^1$ is as hereinbefore defined and Z is a leaving group. Suitably Z is a halo (such as chloro or bromo), tosyl, mesyl or $OSO_3R^1$ group wherein $R^1$ is as hereinbefore defined. Another example of a reagent that provides an $R^1$ group is an alkene derivative such as hexafluoropropylene which, on reaction with a compound of the formula (4), provides the corresponding compound wherein $R^1$ is —$CF_2CHFCF_3$.

An example of $R^9$ being a precursor of the group $R^2$ is when $R^9$ is a cyano group. Such a group can be hydrolysed to a carboxamido group in conventional manner, for example by treatment with concentrated sulphuric acid at moderate temperature or by treatment with aqueous hydrogen peroxide and potassium hydroxide or by treatment with manganese dioxide on silica gel.

A compound of the formula (1) wherein $R^2$ is a cyano group can be converted to the corresponding compound wherein $R^2$ is carboxy by hydrolysis for example using aqueous potassium hydroxide at elevated temperature, for example at the reflux temperature of the the reaction mixture or in a pressure vessel at 100°-160° C.

A compound of the formula (1) wherein $R^2$ is a cyano group can be converted to a compound of formula (1) wherein $R^2$ is 5-tetrazolyl in conventional manner, for example by treatment with a suitable azide salt such as ammonium, sodium, potassium or aluminium azide in a suitable organic solvent such as dimethylformamide, dimethylsulphoxide, N-methylpyrrolidin-2-one or tetrahydrofuran at an elevated temperature e.g. 40°-200° C., preferably at the reflux temperature of the the reaction mixture.

A compound of the formula (1) wherein $R^2$ is carboxy can be esterified to a compound of formula (1) wherein $R^2$ is —$CO_2R^7$ by treatment with $R^7OH$ wherein $R^7$ is as hereinbefore defined in the presence of an acid catalyst.

A compound of the formula (1) wherein $R^2$ is —$CONR^5R^6$ can be prepared by reacting a compound of the formula (1) wherein $R^2$ is —$CO_2R^7$ with an amine: $HNR^5R^6$ wherein $R^5$ and $R^6$ are as hereinbefore defined.

A compound of the formula (1) wherein $R^2$ is hydrogen can be prepared by decarboxylating a compound of the formula (1) wherein $R^2$ is carboxy, for example by heating at elevated temperature in the absence of a solvent or in the presence of a solvent such as quinoline.

Another example of $R^9$ being a precursor to the group $R^2$ is when $R^9$ is a nitro group. Such a group can be reduced to an amino group in conventional manner, for example via catalytic hydrogenation, for example using hydrogen gas or catalytic transfer hydrogenation.

Compounds of the formula (1) wherein $R^2$ is amino can be converted to compounds of the formula (1) wherein $R^2$ is —$NHCOR^8$ by conventional methods of acylation, for example using an acid halide, an acid anhydride or an activated ester.

Compounds of the formula (2) wherein Y is hydroxy can suitably be prepared by reaction under basic conditions of a compound of the formula (5):

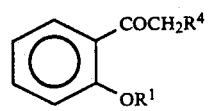

wherein $R^1$ and $R^4$ are as hereinbefore defined, with a compound of the formula R³COL wherein R³ is as hereinbefore defined and L is a leaving group.

Suitably L is ethoxy or methoxy. Conveniently a solution of a compound of the formula (5) and a compound of the formula R³COL in a suitable organic solvent such as diethyl ether is treated with a suitable base such as an alkali metal alkoxide, e.g. sodium methoxide at ambient temperature. The resulting reaction mixture is preferably extracted with water and the aqueous extract with contains the alkali metal salt of a compound of the formula (2) wherein Y is hydroxy is then treated with a compound of the formula (3) as hereinbefore described.

Compounds of the formula (2) wherein Y is a secondary amino group (e.g. dimethylamino) can suitably be prepared by reacting a compound of the formula (5) with a compound of the formula R³C(OR)₂Y wherein R³ is as hereinbefore defined, R is $C_{1-4}$alkyl and Y is a secondary amino group (for example R³C(OR)₂Y is N,N-dimethylformamide dimethyl or diethyl acetal).

A compound of the formula (4) can be prepared by reacting a compound of the formula (6) :

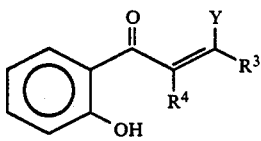 (6)

wherein Y, R³ and R⁴ are as hereinbefore defined, with a compound of the formula (3) as hereinbefore defined in a similar manner as hereinbefore described for the preparation of a compound of the formula (1).

Pharmaceutically acceptable base addition salts of the compounds of the formula (1) may be prepared by standard methods, for example by reacting a solution of the compound of the formula (1) with a solution of the base.

In another aspect this invention provides a compound of the formula (1) as hereinbefore defined and a pharmaceutically acceptable salt thereof, for use as a medicament.

In a further aspect this invention provides a method of effecting bronchodilatation or of combatting allergic disease in a host in need thereof by administration of a non-toxic but effective amount of a compound of the formula (7):

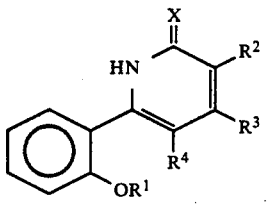 (7)

wherein X, R¹, R², R³ and R⁴ are as hereinbefore defined for a compound of the formula (1) except that R¹ can be methyl when R² is —CO₂H, —CO₂CH₂CH₃ or —CN, X is O, R³ is hydrogen and R⁴ is hydrogen or methyl.

The compounds of the formula (7) can be prepared, formulated as pharmaceutical compositions and used as medicaments in methods of therapy as hereinbefore described for the compounds of formula (1).

The following biological test methods, data and Examples serve to illustrate this invention.

Bronchodilatation—*In vivo*

Male guinea-pigs of the Dunkin Hartley strain (500–600 g) were anaesthetised with Sagatal (pentobarbital sodium) (60 mg/kg). Airway resistance was measured using a modification of the classical Konzett-Rossler technique (J. Pharm. Methods, 13, 309–315, 1985). U46619 (9,11-methanoepoxy-pGH₂) was infused i.v. at a rate of 2.5 nmol/min, this produced a steady state of bronchoconstriction (approximately 120% increase from basal airway resistance). The compound under test was administered by i.v. bolus injection, and the subsequent peak inhibition of bronchoconstriction recorded.

The dose of compound required to reduce the U46619-induced bronchoconstriction by 50% is given as the $BD_{50}$. These results demonstrate in vivo anti-bronchoconstrictor activity.

| COMPOUND | $BD_{50}$ (μmol/kg) |
|---|---|
| Ex 1 | 10.0 |
| Ex 2 | 1.1 |
| Ex 3 | 10.6 |
| Ex 7 | 7.7 |
| Ex 11 | 2.3 |

Vasodilatation—*In vivo*

Male Wistar rats (300 g) were anaesthetised with a sodium 5-ethyl-5-(1-methylpropyl)-2-thiobarbiturate/-sodium pentobarbitone mixture i.p. (62.5 and 22.5 mg/kg respectively). The trachea was cannulated and the rats breathed spontaneously air enriched with O₂ (5 ml/min). Blood pressure was recorded from a carotid artery and a jugular vein was cannulated for the administration of compounds. The temperature of the animal was maintained at 37° C. by the use of an electric blanket. The abdominal aorta was separated from the inferior vena cava, distal to the renal arteries and was cannulated centrally to supply the perfusion pump with blood and distally for the perfusion of the hind quarters at constant pressure. The perfusion circuit was primed with 5% bovine serum albumin dissolved in 0.9% sodium chloride solution, pH adjusted to 7.4. Initially the pump rate was set between 10 and 15 ml/min to match the hind quarter perfusion pressure to that of the systemic circulation. Once set, the pressure remained unaltered for the rest of the experiment. A change in the speed of the pump (equivalent to hindquarter blood flow) was used to assess the changes in hindquarter vascular resistance.

All compounds were administered as a bolus i.v. and from the dose response curves the dose required to produce a 50% increase in hindquarter blood flow ($EDHQ_{50}$) was determined in μmoles/kg. The following results were obtained :

| COMPOUND | $EDHQ_{50}$ (μmol/kg) |
|---|---|
| Ex 1 | 11.5 |
| Ex 2 | 14 |

Anti-Allergic Activity

Male Duncan Hartley guinea-pigs (250–300 g) were sensitised to ovalbumen by i.p. injection of 2 ml of 50 mg.ml⁻¹ i.p. and 0.2 ml s.c. Three weeks later they were anaesthetised with 60 mg.kg$^{-1}$ sodium pentabarbitone. The trachea was cannulated and the animal respired at a rate of 40 breaths per minute and at an initial tracheal inflation pressure of 16 mmHg. Tracheal inflation pressure was measured by a transducer connected to a side arm of the respiration circuit The carotid artery was cannulated for the measurement of blood pressure and the signal was used to trigger an instantaneous rate meter. A jugular vein was cannulated for the administration of drug and allergen. After surgery the animals were allowed to stabilise and the drug was administered i.v. as a bolus. Following this, ovalbumen 1 mg.kg$^{-1}$ was injected i.v. as the antigen challenge either 2, 15 or 30 minutes following drug treatment and the peak bronchoconstrictor response recorded. For the control group ovalbumen only was given. One ovalbumen challenge per guinea-pig was used and n = 6 for each time point. The percentage increase in tracheal inflation pressure was calculated.

The compound of Example 2 at a dose of 11 μmol/kg caused a 44% inhibition of the control bronchoconstrictor response 30 minutes following drug adminstration indicating an anti-allergic activity.

Phosphodiesterase Activity

The activity of the compounds of the present invention as inhibitors of a calmodulin insensitive cyclic GMP phosphodiesterase was measured using the procedure described in European Patent Application No. 293063. The compounds of Examples 1, 2, 4, 6, 7, 9, 11, 12 and 14 had IC$_{50}$ values (the concentration of inhibitor required for 50% inhibition of enzyme activity) in the range 1.7 to 30 μM. The compounds of the present invention have the advantage that they are selective in not inhibiting cyclic AMP phosphodiesterase (type III).

EXAMPLE 1

3-Cyano-6-(2-propoxyphenyl)-2(1H)-pyridinone

A solution of 2-propoxyacetophenone (8.9 g) and ethyl formate (3.7 g) in diethyl ether (45 ml) was added dropwise over one hour to a cooled (<5° C.) suspension of sodium methoxide prepared from sodium hydride (2.4 g, 50% dispersion in oil) and dry methanol (2.05 ml) in anhydrous diethyl ether (45 ml). The mixture was stirred with cooling for 30 minutes and then stirred at ambient temperature overnight. The resulting mixture was extracted with water (4×15 ml) and the combined aqueous extracts were treated with cyanoacetamide (4.2 g) and a solution of glacial acetic acid (0.75 ml), water (3 ml) and piperidine (1.2 ml). The resulting mixture was heated under reflux for 2.5 hours, cooled and acidified with glacial acetic acid to afford a gum. The gum was washed with water and triturated with hot ethanol (40 ml) to afford the title compound as a cream powder, 3.22 g, m.p. 244°-247° C. A sample of this material (1.2 g) was recrystallised twice from dimethylformamide to yield the title compound as a white crystalline solid, 0.94 g, m.p. 245°-7° C.

EXAMPLE 2

6-(2-Propoxyphenyl)-1,2-dihydro-2-oxopyridine-3-carboxamide

30% Hydrogen peroxide (2.5 ml) was added dropwise over 10 minutes to a stirred solution of 3-cyano-6-(2-propoxyphenyl)-2(1H)-pyridinone (1.25 g) and potassium hydroxide (0.55 g) in water (10 ml). The mixture was warmed slightly and diethyl ether was added in order to control considerable frothing that was observed. The reaction mixture was then heated at ca 45° C. for 1.5 hours, cooled and allowed to stand overnight at room temperature. A further sample of 30% hydrogen peroxide (1.5 ml) was added and the procedure as described above was followed until the reaction was complete. The cooled reaction mixture was neutralised with glacial acetic acid to afford a white precipitate (1.2 g) which was collected. This material was eluted from a silica column with dichloromethane/methanol (25:1) and the combined fractions containing product were evaporated to afford a cream coloured powder (0.92 g) which was recrystallised from absolute ethanol (20 ml) to afford the pure title compound, 0.81 g, m.p. 176°-8° C.

EXAMPLE 3

6-(2-Propoxyphenyl)-1,2-dihydro-2-oxopyridine-3-carboxylic acid

A solution of 3-cyano-6-(2-propoxyphenyl)-2(1H)-pyridinone (0.82 g) and absolute ethanol (1 ml) in 5 Normal potassium hydroxide (10 ml) was heated at 140° C. in a steel pressure vessel for 4 hours. The cooled mixture was acidified with concentrated hydrochloric acid to afford a cream solid which was collected. Thin layer chromatography indicated that this solid contained the required product together with an intermediate carboxamido compound and a trace of starting material Thus the solid was redissolved in 5 Normal potassium hydroxide (10 ml) and heated in a steel pressure vessel for 3 hours at 140° C. The cooled mixture was acidified with concentrated hydrochloric acid and the precipitated solid was collected, 0.90 g. The precipitate was recrystallised from aqueous ethanol to afford the title compound, 0.55 g, m.p. 194°-196° C.

EXAMPLE 4

Methyl 6-(2-propoxyphenyl)-1,2-dihydro-2-oxopyridine-3-carboxylate

A stirred mixture of 6-(2-propoxyphenyl)-1,2-dihydro-2-oxopyridine-3-carboxylic acid, (0.9 g) dry methanol (30 ml) and 3 drops of concentrated sulphuric acid was heated under reflux for ca 24 hours. The cooled mixture was evaporated to yield a pale yellow solid which was dissolved in chloroform, extracted with dilute aqueous potassium carbonate (2×10 ml), washed with water and brine, dried (magnesium sulphate) and evaporated to yield a yellow solid, 0.8 g, m.p. 126°-7° C. This was recrystallised from aqueous methanol (20 ml) to yield the pure title compound, 0.65 g, m.p. 126.5°-127.5° C.

EXAMPLE 5

6-(2-Propoxyphenyl)-3-(1H-tetrazol-5-yl)-2(1H)-pyridinone

A stirred mixture of 3-cyano-6-(2-propoxyphenyl)-2-(1H)-pyridinone (1.85 g), sodium azide (0.59 g), ammonium chloride (0.49 g) and lithium chloride (0.39 g) in dry dimethylformamide (75 ml) was heated at 120° C. for 72 hours. The reaction mixture was evaporated to dryness and the resultant residue treated with water (100 ml) and acidified with glacial acetic acid to afford a precipitate which was collected and dissolved in warm dilute aqueous potassium bicarbonate. The aqueous solution was allowed to stand overnight at room temperature, was filtered and the filtrate was acidified with concentrated hydrochloric acid to afford a yellow precipitate, 1.80 g, m.p. 226°-230° C. This was recrystallised from ethanol (with charcoal) to afford the pure title compound, 1.08 g, m.p. 229°-231° C.

EXAMPLE 6

6-(2-Propoxyphenyl)-2(1H)-pyridinone 6-(2-Propoxyphenyl)-1,2-dihydro-2-oxopyridine-3-carboxylic acid (2.25 g) was heated at 300° C. under nitrogen for about 5 minutes. The cooled residue was partitioned between chloroform (50 ml) and dilute aqueous potassium carbonate (30 ml) and a small amount of insoluble material was removed by filtration. The organic phase was washed with dilute aqueous potassium carbonate, water and brine, dried (magnesium sulphate) and evaporated under reduced pressure to afford a yellow powder, 0.42 g. This material together with another sample (50 mg) similarly prepared was recrystallised from cyclohexane/toluene (10:1, 20 ml) to yield a cream solid, 0.27 g which was recrystallised twice from cyclohexane to afford the pure title compound, 0.19 g, m.p. 134°-135.5° C.

EXAMPLE 7

3-Nitro-6-(2-propoxyphenyl)-2(1H)-pyridinone

A solution of 2-propoxyacetophenone (4.45 g) and ethyl formate (2.4 ml) in diethyl ether (20 ml) was added dropwise over 30 minutes to a cooled (< 5° C.) suspension of sodium methoxide prepared from sodium hydride (1.2 g, 50% dispersion in oil) and dry methanol (1 ml) in anhydrous diethyl ether (30 ml). The mixture was stirred with cooling for 30 minutes and then stirred at ambient temperature overnight. The resulting mixture was extracted with water (4×15 ml) and the combined aqueous extracts were treated with nitroacetamide (2.2 g) and a solution of glacial acetic acid (0.5 ml), water (2 ml) and piperidine (0.5 ml). The resulting mixture was heated under reflux for ca 3 hours, cooled and acidified with glacial acetic acid to afford a gum. The gum was washed with water and triturated with warm ethanol (50 ml) to afford the crude title compound as a yellow powder, 0.60 g, m.p. 198°-200° C. This was recrystallised from acetonitrile to afford the pure title compound as yellow needles, 0.5 g, m.p. 201°-3° C.

EXAMPLE 8

3-Cyano-6-(2 methoxyphenyl)-2(1H)-pyridinone a) A stirred mixture of 2-methoxyacetophenone (5.5 ml) and dimethylformamide dimethylacetal (6.7 ml) in dry dimethylformamide (40 ml) was heated under reflux for 18 hours. A further quantity of dimethylformamide dimethylacetal (1 ml) was added and reflux continued for 3 hours. The cooled reaction mixture was diluted with ethyl acetate, washed with water and brine, dried (magnesium sulphate) and evaporated under reduced pressure yielding 3-dimethylamino-1-(2-methoxyphenyl)-2-propene-1-one as an orange oil. Further product remained in the aqueous extract which was evaporated under reduced pressure to yield a residue which was dissolved in ethyl acetate. The filtered solution was washed with water and brine, dried (magnesium sulphate) and evaporated under reduced pressure to yield a further quantity of orange oil. Total yield was 5.74 g.

b) A stirred mixture of 3-dimethylamino-1-(2-methoxyphenyl)-2-propene-1-one (5.74 g), cyanoacetamide (2.48 g) and sodium methoxide (from sodium hydride (50%, 4.32 g) and methanol (3.5 ml)) in dry dimethylformamide was heated under reflux for 10 hours. The reaction mixture was poured into water, acidified to pH4 with glacial acetic acid and extracted with ethyl acetate. The ethyl acetate extract was evaporated under reduced pressure to low volume and water was added to cause precipitation of a crude product (3.67 g) which was collected and recrystallised twice from dimethylformamide to yield the title compound, 1.68 g, m.p. 236°-238° C.

EXAMPLE 9

3-Cyano-6-(2-ethoxyphenyl)-2(1H)-pyridinone

In a similar manner to that of Example 1, 2-ethoxyacetophenone (2 g) yielded the title compound, 0.32 g, m.p. 262°-4° C. (from dimethylformamide).

EXAMPLE 10

3-Amino 6-(2-propoxyphenyl)-2(1H) pyridinone

A solution of 3-nitro-6-(2-propoxyphenyl)-2(1H)-pyridinone (0.3 g) in a mixture of ethanol (20 ml) and water (10 ml) containing 2 Normal sodium hydroxide (0.75 ml) was shaken with 10% palladium on charcoal (0.05 g) under hydrogen at atmospheric pressure until the uptake of hydrogen had ceased. The filtered solution was treated with dilute hydrochloric acid to pH 6 and evaporated to half its volume. Water (5 ml) was added and the mixture was filtered to give a crude product, 0.29 g, m.p. 158°-161° C. Recrystallisation from 50% aqueous ethanol afforded the pure title compound, 0.11 g, m.p. 164.5°-165.5° C.

EXAMPLE 11

3-Cyano-4-methyl-6-(2-propoxyphenyl)-2(1H)-pyridinone

In a similar manner to that of Example 1, 2-propoxyacetophenone (8.9 g) was allowed to react with ethyl acetate in the presence of sodium methoxide, and the intermediate was cyclised with cyanoacetamide to give the title compound, 0.2 g, m.p. 180°-180.5° C. (from acetonitrile).

EXAMPLE 12

3-Cyano-5-methyl-6-(2-propoxyphenyl)-2(1H)-pyridinone

In a similar manner to that of Example 1, 2-propoxypropiophenone (9.6 g) gave the title compound, 3.0 g, m.p. 213°-214 5° C. (from acetonitrile).

EXAMPLE 13

3-Cyano-6-(2-(1,1,2,3,3,3-hexafluoropropoxy)phenyl-2(1H)-pyridinone

A stirred suspension of sodium hydride (0.024 g, 50% in oil) and 3-cyano-6-(2-hydroxyphenyl)-2(1H)-pyridine (1.06 g) in dimethylformamide (10 ml) was warmed to give a clear yellow solution. Hexafluoropropylene was passed through the solution at 10° C. until approximately 0.95 g was absorbed The mixture was stirred at room temperature for 3 hours, allowed to stand overnight, then poured into water to give a solid, 1.69 g. Recrystallisation from acetonitrile afforded the pure title compound, 0.4 g, m.p. 220°-222° C.

The starting material for the above was prepared in a similar manner to that of Example 1. Thus, 2-hydroxyacetophenone (10.2 g) yielded 3-cyano-6-(2-hydroxyphenyl)-2(1H)-pyridinone, 4.4 g, m.p. 317°-320° C. (from aqueous ethanol).

EXAMPLE 14

3-Cyano-6-(2-propoxyphenyl)-2(1H)-pyridinethione

2-Propoxyacetophenone (2.14 g) and dimethylformamide dimethylacetal (2 ml) were heated together in dimethylformamide (10 ml) at 130° C. for 18 hours. Cyanothioacetamide (1.6 g) was added, heating was continued for 2 hours, and then the cool mixture was poured into water (100 ml). The aqueous mixture was neutralised with acetic acid and extracted with ethyl acetate. Evaporation of the extract gave a residue which was purified by medium pressure chromatography (silica, dichloromethane:methanol mixtures) to give a solid, 0.35 g, m.p. 127°-128° C. Recrystallisation from aqueous ethanol afforded the pure title compound, 0.22 g, m.p. 130°-131° C.

EXAMPLE 15

1,2-dihydro-4-methyl-2-oxo-6-(2-propoxyphenyl)pyridine-3-carboxylic acid

A mixture of 3-cyano-4-methyl-6-(2-propoxyphenyl)-2(1H)-pyridinone (0.75 g) and 5 normal potassium hydroxide (15 ml) was heated in a steel pressure vessel at 140° C. for 4 hours, then the cool solution was acidified with hydrochloric acid. A suspension of the resultant solid in aqueous hydrochloric acid (pH 1) was warmed on a steam bath for 20 minutes, cooled, and filtered to afford the title compound, 0.71 g, m.p. 175°-177° C.

EXAMPLE 16

Methyl 1,2-dihydro-4-methyl-2-oxo-6-(2-propoxyphenyl)-pyridine-3-carboxylate

A mixture of 1,2-dihydro-4-methyl-2-oxo-6-(2-propoxyphenyl)pyridine-3-carboxylic acid (0.75 g), methanol (50 ml) and concentrated sulfuric acid (0.5 ml) was heated under reflux for 6 hours. The residue left after evaporation was treated with water (30 ml) and potassium carbonate was added to pH 10. The resultant solid was washed with water and with ether to afford the title compound, 0.6 g, m.p. 167°-169° C.

EXAMPLE 17

1,2-Dihydro-4-methyl-2-oxo-6-(2-propoxyphenyl-)pyridine-3-carboxamide

Methyl 1,2-dihydro-4-methyl-2-oxo-6-(2-propoxyphenyl)-pyridine-3-carboxylate (0.53 g) and saturated methanolic ammonia (25 ml) was heated in a sealed vessel at 70°-85° C. for 34 hours. The residue after evaporation was triturated with methanol (10 ml) to give a solid, 0.28 g, m.p. 239°-242° C. Recrystallisation from ethanol afforded the title compound, 0.18 g, m.p. 244°-246° C.

EXAMPLE 18

3-Cyano-6-(2-cyclopropylmethoxyphenyl)-2(1H)-pyridinone

A stirred mixture of 2-(cyclopropylmethoxy)-acetophenone (15 g), dimethylformamide (45 ml) and dimethylformamide dimethylacetal (12.75 ml) was heated at 140° C. for 25 hours, then cyanoacetamide (8.29 g) was added and the mixture was heated for a further 18 hours. The cool mixture was added to water (200 ml) and diethyl ether (100 ml) and the solid was collected by filtration, washed with water then with ethanol. Digestion with acetonitrile give the title compound, 6.1 g, m.p. 250°-252° C. (from acetonitrile).

EXAMPLE 19

6-(2-Butoxyphenyl)-3-cyano-2(1H)-pyridinone

In a similar manner to that of Example 18, 2-butoxyacetophenone (15.36 g) gave the title compound, 5.56 g, m.p. 218°-219° C. (from acetonitrile).

EXAMPLE 20

6-(2-Allyloxyphenyl)-3-cyano-2(1H)-pyridinone

In a similar manner to that of Example 18, 2-allyloxyacetophenone (15.84 g) gave the title compound, 7.76 g, m.p. 229°-23° C. (from dimethylformamide).

EXAMPLE 21

3-Cyano-6-[2-(2-methylpropoxy)phenyl]-2(1H)-pyridinone

In a manner similar to that of Example 18, 2-(2-methylpropoxy)acetophenone (15 g) gave the title compound, 3.96 g, m.p. 235° C. (from acetonitrile).

EXAMPLE 22

6-(2-Ethoxyphenyl)-1,2-dihydro-2-oxopyridine-3-carboxamide

30% Hydrogen peroxide (12.45 ml) was added during 1 hour to a stirred solution of the product of Example 9 (2 g) and potassium hydroxide (2.24 g) in water (20 ml) at 65+ C. After a further 1 hour the mixture was acidified with hydrochloric acid to give the title compound, 2.06 g, m.p. 218°-220° C. (from ethanol).

EXAMPLE 23

6-(2-Cyclopropylmethoxyphenyl)-1,2-dihydro-2-oxopyridine-3 carboxamide

In a similar manner to that of Example 22, the product of Example 18 (2 g) gave the title compound, 2 g, m.p. 160°-161.5° C. (from acetonitrile).

EXAMPLE 24

6-(2-Butoxyphenyl)-1,2-dihydro-2-oxopridine-3-carboxamide

In a similar manner to that of Example 22, the product of Example 19 (2.01 g) gave the title compound, 2.09 g, m p. 190°-191° C. (from acetonitrile).

EXAMPLE 25

6-(2-Allyloxyphenyl)-1,2-dihydro-2-oxopyridine-3-carboxamide

In a similar manner to that of Example 22, the product of Example 20 (1.89 g) gave the title compound, 1.74 g, m.p. 210°-212° C. (from dimethylformamide).

EXAMPLE 26

6-(2-Methylpropoxyphenyl)-1,2-dihydro-2-oxopyridine-3-carboxamide

A stirred mixture of the product of Example 21 (1.39 g), manganese dioxide on silica gel (9 g) and benzene (150 ml) was heated under reflux overnight. Further manganese dioxide on silica gel (0.9 g) was added and the mixture was heated for another 3 hours. The mixture was filtered and the solid was washed with hot methanol. Evaporation of the benzene and methanol solutions gave the title compound, 1 39 g, m.p. 180° C. (from methanol).

EXAMPLE 27

Pharmaceutical compositions for oral administration are prepared by combining the following :

|  | % w/w | | |
| --- | --- | --- | --- |
| 6-(2-Propoxyphenyl)-1,2-dihydro-2-oxopyridine-3-carboxamide | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 28

A pharmaceutical composition for parenteral administration is prepared by dissolving the title compound of Example 17 (0.02 g) in polyethylene glycol 300 (25 ml) with heating This solution is then diluted with water for injections Ph. Eur. (to 100 ml). The solution is then sterilised by filtration through a 0.22 micron membrane filter and sealed in sterile containers.

EXAMPLE 29

1,2-Dihydro-5-methyl-2-oxo-6-(2-propoxyphenyl)pyridine-3-carboxamide

In a similar manner to that of Example 22, the product of Example 12 (1.50 g) gave the title compound, 0.75 g, m.p. 238.5°–239.5° C. (from acetonitrile).

What is claimed is:

1. A compound of the formula (1):

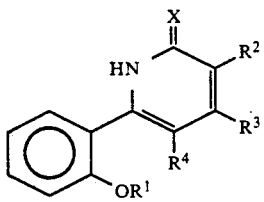

or a pharmaceutically acceptable salt thereof, wherein
X is O or S;
$R^1$ is $C_{2-6}$alkyl, $C_{2-6}$alkenyl, $C_{3-5}$cycloalkyl$C_{1-4}$alkyl, or $C_{1-4}$alkyl substituted by 1 to 6 fluoro groups;
$R^2$ is hydrogen, —CN, —CONR$^5$R$^6$, 5-tetrazolyl, —NO$_2$, or NHCOR$^8$ wherein $R^5$, $R^6$ and $R^8$ are independently hydrogen or $C_{1-4}$alkyl;
$R^3$ is hydrogen or $C_{1-4}$alkyl; and
$R^4$ is hydrogen or $C_{1-4}$alkyl.

2. A compound according to claim 1 wherein X is O.
3. A compound according to claim 1 wherein $R^1$ is $C_{2-6}$alkyl.
4. A compound according to claim 1 wherein $R^1$ is $C_{3-5}$alkenyl.
5. A compound according to claim 1 wherein $R^2$ is hydrogen, —CN, 5-tetrazolyl or —NO$_2$.
6. A compound according to claim 1 wherein $R^2$ is —CONR$^5$R$^6$ wherein —NR$^5$R$^6$ is amino.
7. A compound according to claim 1 wherein $R^3$ is hydrogen or methyl.
8. A compound according to claim 1 wherein $R^4$ is hydrogen or methyl.

9. A compound according to claim 1 which is selected from the group consisting of:
3-cyano-6-(2-propoxyphenyl)-2(1H)-pyridinone,
6-(2-propoxyphenyl)1,2-dihydro-2-oxopyridine-3-carboxamide--,
6-(2-propoxyphenyl)-3-(1H-tetrazol-5-yl)-2(1H)-pyridinone,
3-nitro-6-(2-propoxyphenyl)-2(1H)-pyridinone,
3-cyano-6-(2-ethoxyphenyl)-2(1H)-pyridinone--,
3-cyano-4-methyl-6-(2-propoxyphenyl)-2(1H)-pyridinone,
3-cyano-5-methyl-6-(2-propoxyphenyl)-2(1H)-pyridinone,
-- 3-cyano-6-(2-(1,1,2,3,3,3-hexafluoropropoxy)phenyl)-2(1H)-pyridinone --,
3-cyano-6-(2-propoxyphenyl)-2(1H)-pyridinethione,
1,2-dihydro-4-methyl-2-oxo-6-(2-propoxyphenyl)pyridine-3-carboxamide,
3-cyano-6-(2-cyclopropylmethoxyphenyl)-2(1H)-pyridinone,
6-(2-butoxyphenyl)-3-cyano-2(1H)-pyridinone,
6-(2-allyloxyphenyl)-3-cyano-2(1H)-pyridinone,
3-cyano-6-2(1H)-pyridinone,
6-(2-ethoxyphenyl-1,2-dihydro-2-oxopyridine-3-carboxamide,
6-(2-cyclopropylmethoxyphenyl)-1,2-dihydro-2-oxopyridine-3-carboxamide,
6-(2-butoxyphenyl)-1,2-dihydro-2-oxopyridine-3-carboxamide,
6-(2-allyloxyphenyl)-1,2-dihydro-2-oxopyridine-3-carboxamide, or
--6-(2(2-methylpropoxy)phenyl)-1,2-dihydro-2-oxopyridine-3-carboxamide,
or a pharmaceutically acceptable salt thereof.

10. A pharmaceutical composition for effecting bronchodilatation which comprises a compound according to claim 1 and a pharmaceutically acceptable carrier.

11. A pharmaceutical composition having anti-allergic activity which comprises a compound according to claim 1 and a pharmaceutically acceptable carrier.

12. A method of effecting bronchodilatation in a host in need thereof by administration of a non-toxic but effective amount of a compound of the formula (7):

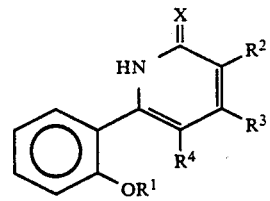

-- or a pharmaceutically acceptable salt thereof, wherein
X is O or S;
$R^1$ is $C_{1-6}$alkyl, $C_{2-6}$alkenyl, $C_{3-5}$cycloalkyl$C_{1-4}$alkyl, or $C_{1-4}$alkyl substituted by 1 to 6 fluoro groups;
$R^2$ is hydrogen, —CN, —CONR$^5$R$^6$, —CO$_2$R$^7$, 5-tetrazolyl, —NO$_2$, NH$_2$ or NHCOR$^8$ wherein $R^5$, $R^6$, $R^7$ and $R^8$ are independently hydrogen or $C_{1-4}$alkyl;
$R^3$ is hydrogen or $C_{1-4}$alkyl; and
$R^4$ is hydrogen or $C_{1-4}$alkyl.

13. A method of combatting allergic disease in a host in need thereof by administration of a non-toxic but effective amount of a compound of the formula (7) as defined in claim 12.

* * * * *